United States Patent [19]

Bacca et al.

[11] Patent Number: 5,733,530
[45] Date of Patent: Mar. 31, 1998

[54] TARTAR CONTROL DENTIFRICE COMPOSITION CONTAINING THYMOL

[75] Inventors: Lori Ann Bacca, Lebanon; Anthony Charles Lanzalaco, Fairfield, both of Ohio

[73] Assignee: The Procter & Gamble Company, Cincinnati, Ohio

[21] Appl. No.: 706,380

[22] Filed: Aug. 30, 1996

Related U.S. Application Data

[63] Continuation of Ser. No. 175,000, Dec. 29, 1993, abandoned.

[51] Int. Cl.$^6$ ............................... A61K 7/16; A61K 7/18; A61K 7/26
[52] U.S. Cl. ........................... 424/52; 424/49; 424/57
[58] Field of Search ................................ 424/49–58

[56] References Cited

U.S. PATENT DOCUMENTS

| | | | |
|---|---|---|---|
| 2,946,725 | 7/1960 | Norris et al. | 167/93 |
| 4,022,880 | 5/1977 | Vinson et al. | 424/49 |
| 4,254,101 | 3/1981 | Denny, Jr. | 424/52 |
| 4,314,990 | 2/1982 | Denny, Jr. et al. | 424/52 |
| 4,550,018 | 10/1985 | Ambike et al. | 424/52 |
| 4,656,031 | 4/1987 | Lane et al. | 424/49 |
| 4,830,221 | 5/1989 | Mazzanobile | 222/92 |
| 4,885,155 | 12/1989 | Parran, Jr. et al. | 424/52 |
| 4,894,220 | 1/1990 | Nabi et al. | 424/52 |
| 4,906,456 | 3/1990 | Gaffar et al. | 424/52 |
| 4,925,655 | 5/1990 | Smigel et al. | 424/52 |
| 4,945,087 | 7/1990 | Talwar et al. | 514/60 |
| 4,980,153 | 12/1990 | Jackson et al. | 424/52 |
| 5,004,597 | 4/1991 | Majeti et al. | 424/52 |
| 5,094,843 | 3/1992 | Mazzanobile | 424/52 |
| 5,180,578 | 1/1993 | Gaffar et al. | 474/52 |
| 5,296,214 | 3/1994 | Gappar, II | 424/49 |
| 5,328,682 | 7/1994 | Pullen et al. | 424/49 |
| 5,356,615 | 10/1994 | Gaffar | 424/49 |

FOREIGN PATENT DOCUMENTS

| | | | |
|---|---|---|---|
| 244363 | 4/1987 | European Pat. Off. | |
| 0251591 | 1/1988 | European Pat. Off. | A61K 7/16 |
| 0497476 | 8/1992 | European Pat. Off. | A61K 7/16 |
| 3702983 | 12/1987 | Germany. | |
| 2200551 | 8/1988 | United Kingdom | A61K 7/16 |

OTHER PUBLICATIONS

Abstract of Tanpei Seiyako JP 56139415 (Oct. 30, 1981).
Reg. T.M. 240162 Registered Mar. 1, 1881 Listerine Antiseptic Toothpaste furc. May 1881.
Reg. T.M. 118052 Registered Aug. 14, 1917 Listerine Toothpaste furc. Oct. 1912.
Hugo, W. B. and A. D. Russell, "Chemical Disinfectants, Antiseptics and Preservatives", Types of Compound, Pharmaceutical Microbiolgy, Third Ed., Chapter 10, 213–214.
Arctander (1969) Perfumes Flavor Chemicals, II, #2944: Thymol.
Derwent Abstract of Tandei Seiyaku JP 56139415 (Oct. 30, 1981) (thymol in propylene glycol solvent with carboxyvinyl polymer to adhere tightly (in presence of moisture) to dental caries, or tooth root, in treatment of periodontitis dental caries.

*Primary Examiner*—Shep K. Rose
*Attorney, Agent, or Firm*—Angela M. Stone; Mary Catherine Hentz; Douglas C. Mohl

[57] ABSTRACT

Disclosed are tartar control dentifrice compositions containing certain ranges of thymol. These compositions can also include propylene glycol and/or one or more antibacterial agents.

4 Claims, No Drawings

TARTAR CONTROL DENTIFRICE COMPOSITION CONTAINING THYMOL

This is a continuation of application Ser. No. 08/175,000, filed on Dec. 29, 1993, now abandoned.

BACKGROUND OF THE INVENTION

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel, and dentin. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. This is undesirable from an aesthetic standpoint.

Mechanical removal of calculus periodically by the dentist is routine dental office procedure. A variety of chemical and biological agents have also been suggested to retard calculus formation or to remove calculus after it is formed. Pyrophosphate salts are chemical agents known to have the ability to retard calculus formation as described, for example, in U.S. Pat. No. 4,999,184, to Parran, Jr. et al., issued Mar. 12, 1991, the disclosures of which are incorporated herein by reference in their entirety.

It has been discovered by the present invention that oral tartar control compositions can be formulated to include thymol flavor. Thymol is known to have some antimicrobial properties. Therefore the present tartar contol compositions may have some antimicrobial properties. It has also been discovered that these thymol and tartar control agent-containing compositions can also contain propylene glycol and/or one or more antibacterial agents.

It is therefore an object of the invention to provide a tartar control composition which contains thymol. It is also an object of the invention to provide a tartar control composition containing thymol, propylene glycol and/or one or more antibacterial agents.

These and other objects of the present invention will become readily apparent from the detailed description which follows.

All percentages and ratios used herein are by weight, and all measurements are made at 25C, unless otherwise specified.

SUMMARY OF THE INVENTION

The present invention relates to an oral composition comprising from about 3200 ppm to about 4500 ppm of thymol, from about 1.5% to about 10% of one or more water soluble alkali metal pyrophosphate ion source, from about 10 ppm to about 3500 ppm of a water soluble fluoride ion source, and from about 89% to about 98% of one or more carrier materials.

The present invention also relates to an oral composition comprising from about 3000 ppm to about 4000 ppm thymol, from about 0.05% to about 10% propylene glycol, from about 1.5% to about 10% of one or more water soluble alkali metal pyrophosphate ion source, from about 10 ppm to about 3500 ppm of a water soluble fluoride ion source, and from about 79% to about 98% of one or more carrier materials.

DETAILED DESCRIPTION OF THE INVENTION

The present invention relates to oral tartar control compositions comprising thymol. These compositions can also include propylene glycol and/or one or more antibacterial agents.

The oral compositions of the present invention may be in the form of a toothpaste, mouthrinse, and liquid dentifrice. The term "toothpaste", as used herein, means paste, powder, or gel formulations unless otherwise specified.

The term "oral composition" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

The term "carrier materials" as used herein means any material safe and effective for use in the compositions of the present invention. Such materials include thickening materials, humectants, water, buffering agents, abrasive polishing materials, sodium bicarbonate, titanium dioxide, surfactants, flavors, sweeteners, coloring agents, and mixtures thereof.

The present compositions comprise several essential components, as well as optional components. A detailed description of these components are described hereinafter.

Thymol

The present compositions comprise thymol. Thymol, also known as 5-methyl-2-(1-methylethyl)phenol, is used as a flavoring agent and has antimicrobial properties. Thymol is described in more detail in *The Merck Index*, 10th Edition, published by Merck & Co., No. 9246, (1983), incorporated herein by reference in its entirety. The present compositions typically comprise thymol at a level of from about 3000 ppm to about 4500 ppm, and preferably from about 3200 ppm to about 4000 ppm, by weight of the composition.

Soluble Pyrophosphate Ion Source

The soluble alkali metal pyrophosphate ion source used in the present compositions can be any of the alkali metal pyrophosphate salts. Specific salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. [Pyrophosphate salts are described in more detail in Kirk & Othmer, *Encyclopedia of Chemical Technology*, Second Edition, Volume 15, Interscience Publishers (1968), incorporated herein by reference in its entirety.]

The amount of tetrasodium pyrophosphate salt useful in these compositions is any amount effective for tartar control and is generally enough to provide at least about 1.0% $P_2O_7^{-4}$, preferably from about 1.5% to about 10% more preferably from about 3.0% to about 6% by weight of the compositions. It is to be appreciated that the level of $P_2O_7^{-4}$ is that amount capable of being provided to the composition (i.e., the theoretical amount at an appropriate pH) and that other pyrophosphate forms (e.g., $HP_2O_7$) may be present when a final product pH is established.

Optional tartar control agents include such known materials as synthetic anionic polymers [including polyacrylates and copolymers of maleic anhydride or acid and methyl vinyl ether (e.g., Gantrez), as described for example in U.S. Pat. No. 4,627,977 to Gaffar et al., the disclosures of which are incorporated herein by reference in their entirety; as well as, e.g., polyamino propane sulfonic acid (AMPS)], zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

Soluble Fluoride Ion Source:

A soluble fluoride ion source is also incorporated in the invention compositions. The soluble fluoride ion source is used in amounts sufficient to provide from about 10 to about 3500 ppm of the fluoride ion. Preferred fluorides are sodium fluoride, stannous fluoride, indium fluoride, and sodium monofluorophosphate. Norris et al., U.S. Pat. No. 2,946,735, issued Jul. 26, 1960 and Widder et al., U.S. Pat. No. 3,678,154, issued Jul. 18, 1972 disclose such salts as well as others. Both patents are incorporated herein by reference in their entirety.

Antibacterial Agents

The present compositions can include one or more antibacterial agents which are noncationic and substantially water insoluble. An antibacterial agent which is substantially water insoluble as described herein means that its solubility is less than about 1% by weight in water at 25C and may be even less than about 0.1%. If an ionizable group is present, solubility is determined at a pH at which ionization does not occur.

Examples of noncationic water insoluble antimicrobial agents useful in the present compositions include halogenated diphenyl ethers (excluding 2',4,4'-trichloro-2-hydroxy-diphenyl ether), phenolic compounds including phenol and its homologs, mono and poly-alkyl and aromatic halophenols, resorcinol and its derivatives, bisphenolic compounds and halogenated salicylanilides, benzoic esters, and halogenated carbanilides. Antibacterial agents can be present in an effective antiplaque amount, typically about 0.01% to about 5% by weight of the compositions.

Solubilizing Agent

The present compositions also contain a solubilizing agent. Suitable solubilizing agents solubilize thymol and/or any antibacterial agents and do not adversely affect the activity of thymol and the antibacterial agents used in the compositions. Solubilizing agents useful in the present compositions include propylene glycol, dipropylene glycol, methyl cellosolve, ethyl cellosolve, olive oil, castor oil, amyl acetate, ethyl acetate, glyceryl tristearate and benzyl benzoate. Preferred is propylene glycol. Solubilizing agents are typically used at a level of from about 0.05% to about 10% by weight of the compositions.

Carrier Materials

In preparing the present compositions, it is desirable to add one or more carrier materials to the compositions. Such materials are well known in the art and are readily chosen by one skilled in the art based on the physical and aesthetic properties desired for the composition being prepared. Carrier materials typically comprise from about 79% to about 98%, preferably from about 89% to about 98%, by weight of the compositions.

The present invention compositions, such as toothpastes, typically contain some thickening material or binders to provide a desirable consistency. Preferred thickening agents are carboxyvinyl polymers (such as polyacrylic acids crosslinked with polyallyl sucrose or pollyallyl pentaerythritol), carrrageenan, hydroxyethyl cellulose and water soluble salts of cellulose ethers such as sodium carboxymethyl cellulose, sodium carboxymethyl hydroxyethyl cellulose, and mixtures thereof. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an amount from about 0.1% to about 5% by weight of the total composition.

It is also desirable to include some humectant material in a toothpaste to keep the composition from hardening upon exposure to air. Certain humectants can also impart a desirable sweetness or flavor to the compositions. Suitable humectants include polyethylene glycol, sorbitol, glycerin, xylitol, other edible polyhydric alcohols, and mixtures thereof, at a level of from about 15% to about 70%, by weight of the compositions.

Titanium dioxide may also be added to the present compositions. Titanium dioxide is a white powder which adds pigment to the compositions. Titanium dioxide generally comprise from about 0.25% to about 1% by weight of the compositions.

Water is also present in the toothpaste compositions. Water employed in the preparation of commercially suitable oral compositions should preferably be deionized and free of organic impurities. Water generally comprises from about 5% to about 50%, preferably from about 20% to about 40%, by weight of the toothpaste compositions herein. These amounts of water include the free water which is added plus that which is introduced with other materials such as with sorbitol.

The pH of the present compositions is preferably adjusted through the use of buffering agents. Buffering agents, as used herein, refer to agents that can be used to adjust the pH of the compositions to a range of about pH 7 to about pH 9. These agents include mono and trisodium phosphate, sodium hydroxide, sodium carbonate, tris(hydroxymethyl) aminomethane, tetra and disodium pyrophosphate and tetrapotassium pyrophosphate. Citric acid and sodium titrate are preferred at a level of from about 0.5% to about 10% by weight of the present compositions.

An abrasive polishing material is also included in the toothpaste compositions. The abrasive polishing material contemplated for use in the compositions of the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives of various types are preferred because of their unique benefits of exceptional dental cleaning and polishing performance without unduly abrading tooth enamel or dentin. The silica abrasive polishing materials useful herein, as well as other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975, both incorporated herein by reference. Preferred are the silica xerogels marketed under the tradename "Syloid" by W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, Jul. 29, 1982, incorporated herein by reference. The abrasive in the toothpaste compositions described herein is preferably present at a level of from about 6% to 70% by weight of the compositions.

Sodium bicarbonate can also be added to the present compositions. Sodium bicarbonate, also known as baking soda, is a household product with a variety of uses including use in dentrifices and mouthrinses. It is a white powder that is soluble in water and unless stabilized, tends to release carbon dioxide in an aqueous system. The present compositions can contain from about 1% to about 50%, sodium bicarbonate by weight of the composition.

The present toothpaste compositions can also contain surfactants. Suitable surfactants are those which are reasonably stable and foam throughout a wide pH range, including non-soap anionic, nonionic, cationic, zwitterionic and amphoteric organic synthetic detergents. Many of these suitable agents are disclosed by Gieske et al. in U.S. Pat. No. 4,051,234, Sep. 27, 1977, incorporated herein by reference. Sodium alkyl sulfate and polyethylene glycol are preferred for use in the present compositions at a level of from about 0.5% to about 10% by weight of the compositions.

Flavoring agents in addition to thymol can also be added to the present compositions. Examples of flavoring agents useful in the present invention include oil of peppermint, oil of sassafras, clove bud oil, peppermint, menthol, anethole, methyl salicylate, eucalyptol, cassia, 1-menthyl acetate, sage, eugenol, parsley oil, oxanone, oil of wintergreen, alpha-irisone, oil of spearmint, marjoram, lemon, orange, propenyl guaethol, cinnamin, and mixtures thereof. Flavoring agents are generally used in toothpastes at levels of from about 0.001% to about 5% by weight of the composition.

Sweetening agents can be added to the present compositions. These include aspartame, acesulfame, sodium saccharin, dextrose, sucrose, lactose, maltese, xylitol, levulose, sodium cyclamate and mixtures thereof. Various coloring agents may also be incorporated in the present compositions. Sweetening agents and coloring agents are generally used in toothpastes at levels of from about 0.005% to about 2% by weight of the composition.

The present compositions can be in the form of a mouth rinse or liquid dentifrice where conventional mouth rinse components comprise the carrier materials of the present invention. Mouth rinses and liquid dentifrices generally comprise from about 20:1 to about 2:1 of a water ethyl alcohol or alcohol free solution, and preferably other ingredients such as flavors, sweeteners, humectants, and surfactants such as those mentioned above. The humectants, such as glycerin and sorbitol give a moist feel to the mouth. Generally on a weight basis, the mouth rinses and liquid dentifrices of the present invention comprise from about 0% to about 60% ethyl alcohol, from about 0% to about 20% humectant, from about 0% to about 2% surfactant, from about 0% to about 0.5% sweetening agent, from about 0% to about 0.3% flavoring agent and the balance water. Other optional components described herein for use in toothpaste products are also useful in the mouth rinse and liqiud dentifrice compositions.

The following examples further describe and demonstrate embodiments within the scope of the present invention. These examples are given solely for the purpose of illustration and are not to be construed as limitations of the present invention as many variations thereof are possible without departing from the spirit and scope.

EXAMPLE I

| Tartar Control Formulations Containing Thymol | |
| --- | --- |
| Ingredient | % |
| Sorbitol (70%) | 24.385 |
| Water | 23.080 |
| Silica | 22.000 |
| Glycerin | 9.000 |
| Tetrapotassium pyrophosphate (60%) | 6.382 |
| Sodium alkyl sulfate (27.9%) | 4.000 |
| Polyethylene glycol 300 | 3.000 |
| Disodium pyrophosphate | 2.100 |
| Tetrasodium pyrophosphate | 2.050 |
| Flavor(a) | 2.000 |
| Xanthan gum | 0.600 |
| Titanium dioxide | 0.500 |
| Sodium saccharin | 0.460 |
| Sodium fluoride | 0.243 |
| Carbopol 956(b) | 0.200 |
| (a)Flavor Formulation | % |
| Thymol | 18.780 |
| Other flavors | 40.610 |
| Propylene glycol | 40.610 |

(b)Carbomer 956, supplied by B. F. Goodrich.

EXAMPLE II

| Tartar Control Formulations Containing Thymol | |
| --- | --- |
| Ingredient | % |
| Sorbitol (70%) | 24.385 |
| Water | 23.080 |
| Silica | 22.000 |
| Glycerin | 4.000 |
| Tetrapotassium pyrophosphate (60%) | 6.382 |
| Propylene glycol | 5.000 |
| Sodium alkyl sulfate (27.9%) | 4.000 |
| Polyethylene glycol 300 | 3.000 |
| Disodium pyrophosphate | 2.100 |
| Tetrasodium pyrophosphate | 2.050 |
| Flavor(a) | 2.000 |
| Xanthan gum | 0.600 |
| Titanium dioxide | 0.500 |
| Sodium saccharin | 0.460 |
| Sodium fluoride | 0.243 |
| Carbopol 956(b) | 0.200 |
| (a)Flavor Formulation | % |
| Propylene glycol | 40.000 |
| Thymol | 17.500 |
| Other flavors | 42.500 |

(b)Carbomer 956, supplied by B. F. Goodrich.

Example I and II are prepared as follows. Heat water to about 150F and add sorbitol, saccharin and sodium fluoride. Mix thoroughly. Next add and mix in tetrasodium pyrophosphate, polyethylene glycol and glycerin. Next add disodium pyrophosphate, tetrapotassium pyrophosphate and titanium oxide and mix. Next add flavor and sodium alkyl sulfate and mix until visually dispersed. Then slowly add and thoroughly mix in xanthan gum, carbopol and silica.

What is claimed is:

1. A toothpaste composition consisting essentially of:
   (a) from about 3500 ppm to about 4500 ppm of thymol;
   (b) at least about 1.0% by weight of one or more soluble alkali metal pyrophosphate ion source;

(c) a water soluble fluoride ion source sufficient to provide from about 10 ppm to about 3500 ppm of the fluoride ion; and (d) from about 79% to about 98%, by weight of carrier materials suitable for use in said toothpaste compositions.

2. A toothpaste composition according to claim 1 wherein the toothpaste composition further consists essentially of from about 0.05% to about 10% by weight of a solubilizing agent selected from the group consisting of propylene glycol, dipropylene glycol, methyl cellosolve, ethyl cellosolve, olive oil, caster oil, amyl acetate, ethyl acetate, glyceryl tristerate, benzyl benzoate, and mixtures thereof.

3. A toothpaste composition according to claim 2 wherein the fluoride ion source is selected from the group consisting of sodium fluoride, stannous fluoride, and mixtures thereof.

4. A toothpaste composition according to claim 2 wherein the soluble alkali metal pyrophosphate ion source is selected from the group consisting of diakali metal, tetra alkali metal, and mixtures of diakali and tetra alkali metal pyrophosphate salts.

* * * * *